US011918182B2

(12) United States Patent
McLawhorn

(10) Patent No.: US 11,918,182 B2
(45) Date of Patent: Mar. 5, 2024

(54) CAP FOR ATTACHMENT TO AN ENDOSCOPE

(71) Applicant: Cook Medical Technologies LLC, Bloomington, IN (US)

(72) Inventor: Tyler E. McLawhorn, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 171 days.

(21) Appl. No.: 16/942,291

(22) Filed: Jul. 29, 2020

(65) Prior Publication Data

US 2020/0352416 A1 Nov. 12, 2020

Related U.S. Application Data

(63) Continuation of application No. 13/586,643, filed on Aug. 15, 2012, now abandoned.

(Continued)

(51) Int. Cl.
*A61B 1/00* (2006.01)
*A61B 1/273* (2006.01)

(52) U.S. Cl.
CPC ...... *A61B 1/00089* (2013.01); *A61B 1/00087* (2013.01); *A61B 1/00101* (2013.01); *A61B 1/0014* (2013.01); *A61B 1/2736* (2013.01)

(58) Field of Classification Search
CPC ............ A61B 1/00089; A61B 1/00101; A61B 1/00135; A61B 1/0014; A61B 1/00142;
(Continued)

(56) References Cited

U.S. PATENT DOCUMENTS

| 1,056,336 A | 3/1913 | Hurdman |
| 4,074,718 A | 2/1978 | Morrison, Jr. |

(Continued)

FOREIGN PATENT DOCUMENTS

| JP | 2009 183581 A | 8/2009 | |
| JP | 2010017289 A | * 1/2010 | ......... A61B 1/00087 |

(Continued)

OTHER PUBLICATIONS

International Search Report dated Oct. 15, 2012 for International Application No. PCT/US2012/050516.

(Continued)

*Primary Examiner* — Ryan N Henderson
(74) *Attorney, Agent, or Firm* — Crowell & Moring LLC

(57) ABSTRACT

A cap for attachment to a distal end of an endoscope and a method of positioning the cap on the endoscope are provided. The cap includes a tubular body having a proximal portion, a distal portion and a lumen extending therethrough. The proximal portion includes a first portion and a second portion where at least one of the first portion and the second portion includes a connector for operably connecting the first portion and the second portion. The cap has in open configuration wherein at least a portion of the first portion and the second portion are spaced apart and movable relative to each other. The cap also has a closed configuration wherein the first and second portions are connected and the lumen if formed therethrough. The cap in the closed configuration is sized and shaped to be positionable on the distal end of the endoscope.

14 Claims, 9 Drawing Sheets

Related U.S. Application Data

(60) Provisional application No. 61/525,380, filed on Aug. 19, 2011.

(58) Field of Classification Search
CPC ............ A61B 1/00154; A61B 1/00131; A61B 1/00137; A61B 1/00087; A61B 18/1492
See application file for complete search history.

(56) References Cited

U.S. PATENT DOCUMENTS

| | | |
|---|---|---|
| 4,386,752 A | 6/1983 | Pavlak et al. |
| 4,522,205 A | 6/1985 | Taylor et al. |
| 4,532,924 A | 8/1985 | Auth et al. |
| 4,706,667 A | 11/1987 | Roos |
| 4,765,331 A | 8/1988 | Petruzzi et al. |
| 4,823,791 A | 4/1989 | D'Amelio et al. |
| 4,936,842 A | 6/1990 | D'Amelio et al. |
| 5,100,402 A | 3/1992 | Fan |
| 5,197,491 A | 3/1993 | Anderson et al. |
| 5,254,121 A | 10/1993 | Manevitz et al. |
| 5,259,366 A * | 11/1993 | Reydel ............... A61B 17/221 383/203 |
| 5,443,470 A | 8/1995 | Stern et al. |
| 5,454,809 A | 10/1995 | Janssen |
| 5,494,483 A | 2/1996 | Adair |
| 5,514,130 A | 5/1996 | Baker |
| 5,562,703 A | 10/1996 | Desai |
| 5,575,788 A | 11/1996 | Baker et al. |
| 5,681,282 A | 10/1997 | Eggers et al. |
| 5,683,385 A | 11/1997 | Kortenbach et al. |
| 5,707,355 A | 1/1998 | Zimmon |
| 5,718,702 A | 2/1998 | Edwards |
| 5,743,870 A | 4/1998 | Edwards |
| 5,766,168 A | 6/1998 | Mantell |
| 5,836,906 A | 11/1998 | Edwards |
| 5,906,587 A | 5/1999 | Zimmon |
| 5,925,044 A | 7/1999 | Hofmann et al. |
| 5,957,863 A | 9/1999 | Koblish et al. |
| 5,993,446 A | 11/1999 | Sutter |
| 5,994,717 A | 11/1999 | Igarashi et al. |
| 6,009,877 A | 1/2000 | Edwards |
| 6,027,499 A | 2/2000 | Johnston et al. |
| 6,044,846 A | 4/2000 | Edwards |
| 6,050,993 A | 4/2000 | Tu et al. |
| 6,053,172 A | 4/2000 | Hovda et al. |
| 6,056,744 A | 5/2000 | Edwards |
| 6,059,719 A | 5/2000 | Yamamoto et al. |
| 6,073,052 A | 6/2000 | Zelickson et al. |
| 6,077,257 A | 6/2000 | Edwards et al. |
| 6,086,585 A | 7/2000 | Hovda et al. |
| 6,091,995 A | 7/2000 | Ingle et al. |
| 6,112,123 A | 8/2000 | Kelleher et al. |
| 6,149,647 A | 11/2000 | Tu et al. |
| 6,156,032 A | 12/2000 | Lennox |
| 6,190,381 B1 | 2/2001 | Olsen et al. |
| 6,197,022 B1 | 3/2001 | Baker |
| 6,210,409 B1 | 4/2001 | Ellman et al. |
| 6,231,571 B1 | 5/2001 | Ellman et al. |
| 6,245,067 B1 | 6/2001 | Tu et al. |
| 6,258,084 B1 | 7/2001 | Goldman et al. |
| 6,346,105 B1 | 2/2002 | Tu et al. |
| 6,352,533 B1 | 3/2002 | Ellman et al. |
| 6,355,032 B1 | 3/2002 | Hovda et al. |
| 6,363,937 B1 | 4/2002 | Hovda et al. |
| 6,394,949 B1 | 5/2002 | Crowley et al. |
| 6,402,744 B2 | 6/2002 | Edwards et al. |
| 6,405,732 B1 | 6/2002 | Edwards et al. |
| 6,419,673 B1 | 7/2002 | Edwards et al. |
| 6,464,697 B1 | 10/2002 | Edwards et al. |
| 6,494,881 B1 | 12/2002 | Bales et al. |
| 6,535,764 B2 | 3/2003 | Imran et al. |
| 6,535,768 B1 | 3/2003 | Baker et al. |
| 6,544,226 B1 * | 4/2003 | Gaiser ............... A61B 1/00089 604/113 |
| 6,544,261 B2 | 4/2003 | Ellsberry et al. |
| 6,587,731 B1 | 7/2003 | Ingle et al. |
| 6,589,238 B2 | 7/2003 | Edwards et al. |
| 6,591,838 B2 | 7/2003 | Durgin |
| 6,632,193 B1 | 10/2003 | Davison et al. |
| 6,659,106 B1 | 12/2003 | Hovda et al. |
| 6,669,687 B1 | 12/2003 | Saadat |
| 6,685,713 B1 | 2/2004 | Ahmed |
| 6,692,490 B1 | 2/2004 | Edwards |
| 6,712,814 B2 | 3/2004 | Edwards et al. |
| 6,740,082 B2 | 5/2004 | Shadduck |
| 6,746,447 B2 | 6/2004 | Davison et al. |
| 6,763,836 B2 | 7/2004 | Tasto et al. |
| 6,846,312 B2 | 1/2005 | Edwards et al. |
| 6,872,206 B2 | 3/2005 | Edwards et al. |
| 6,918,906 B2 | 7/2005 | Long |
| 6,932,812 B2 | 8/2005 | Crowley et al. |
| 6,994,705 B2 | 2/2006 | Nobis et al. |
| 7,022,105 B1 | 4/2006 | Edwards |
| 7,025,768 B2 | 4/2006 | Elliott |
| 7,097,644 B2 | 8/2006 | Long |
| 7,137,981 B2 * | 11/2006 | Long ............... A61B 18/1492 606/41 |
| 7,232,438 B2 | 6/2007 | Long |
| 7,252,665 B2 | 8/2007 | Starkebaum et al. |
| 7,344,535 B2 | 3/2008 | Stern et al. |
| 7,442,191 B2 | 10/2008 | Hovda et al. |
| 7,530,979 B2 | 5/2009 | Ganz et al. |
| 7,566,300 B2 | 7/2009 | Devierre et al. |
| 7,648,500 B2 | 1/2010 | Edwards et al. |
| 7,655,004 B2 | 2/2010 | Long |
| 7,658,738 B2 | 2/2010 | Nobis et al. |
| 7,662,151 B2 | 2/2010 | Crompton, Jr. et al. |
| 7,678,069 B1 | 3/2010 | Baker et al. |
| 7,691,101 B2 | 4/2010 | Davison et al. |
| 7,703,459 B2 | 4/2010 | Saadat et al. |
| 7,749,159 B2 | 7/2010 | Crowley et al. |
| 7,758,087 B2 | 7/2010 | Niven et al. |
| 8,105,230 B2 * | 1/2012 | Honda ............... A61B 90/98 600/106 |
| 8,998,897 B2 * | 4/2015 | Binmoeller ........ A61B 1/00131 606/41 |
| 2001/0053909 A1 * | 12/2001 | Nakada ............... A61B 1/00089 606/46 |
| 2002/0177847 A1 * | 11/2002 | Long ............... A61B 18/1492 606/46 |
| 2002/0183739 A1 * | 12/2002 | Long ............... A61B 18/1492 606/41 |
| 2003/0181900 A1 | 9/2003 | Long |
| 2003/0195387 A1 * | 10/2003 | Kortenbach ........ A61B 1/0014 600/104 |
| 2003/0216727 A1 * | 11/2003 | Long ............... A61B 18/1492 606/41 |
| 2005/0080412 A1 | 4/2005 | Ouchi |
| 2006/0167451 A1 | 7/2006 | Cropper |
| 2006/0217698 A1 | 9/2006 | Starkebaum et al. |
| 2006/0258906 A1 * | 11/2006 | Binmoeller ............ A61B 1/012 600/114 |
| 2007/0100201 A1 * | 5/2007 | Komiya ............... A61B 1/00133 600/106 |
| 2007/0212926 A1 * | 9/2007 | Nakaura ................ A61B 1/005 439/465 |
| 2008/0103357 A1 | 5/2008 | Zeiner et al. |
| 2008/0200912 A1 | 8/2008 | Long |
| 2008/0242932 A1 * | 10/2008 | Carter ............... A61B 1/00135 600/127 |
| 2009/0221872 A1 | 9/2009 | Liddle et al. |
| 2009/0270856 A1 | 10/2009 | Saadat et al. |
| 2010/0087813 A1 | 4/2010 | Long |
| 2010/0256632 A1 | 10/2010 | Crowley et al. |
| 2013/0046300 A1 * | 2/2013 | Binmoeller ........ A61B 18/1492 606/41 |
| 2013/0131452 A1 * | 5/2013 | Kuroda ............... A61B 1/00103 600/136 |
| 2017/0065155 A1 * | 3/2017 | Farhadi ............... A61B 1/00154 |

(56) References Cited

U.S. PATENT DOCUMENTS

FOREIGN PATENT DOCUMENTS

| WO | WO 1998/022184 | 5/1998 |
| WO | WO 1999/035987 | 7/1999 |
| WO | WO 2000/019926 | 4/2000 |
| WO | WO 01/68015 A1 | 9/2001 |
| WO | WO 2006/122279 A2 | 11/2006 |

OTHER PUBLICATIONS

Written Opinion of the International Searching Authority dated Oct. 15, 2012 for International Application No. PCT/US2012/050516.

R. Ackroyd et al., "Ablation treatment for Barrett oesophagus: what depth of tissue destruction is needed?," Clin Pathol, 1999;vol. 52, pp. 509-512.

C. P. Barham et al., "Photothermal laser ablation of Barrett's oesophagus: endoscopic and histological evidence of squamous re-epithelialisation," Gut, 1997, vol. 41, pp. 281-284.

R. M. Bremner et al., "Ultrasonic epithelial ablation of the lower esophagus without stricture formation," Surigical Endoscopy, 1998, vol. 12, pp. 342-347.

Gossner et al., "KTP laser destruction of dysplasia and early cancer in columnar-lined Barrett's esophagus," Gastointestinal Endoscopy, Jan. 1999, vol. 49, Issue 1. pp. 8-12.

H. Inoue et al., "Endoscopic mucosal resection with a cap-fitted panendoscope for esophagus, stomach, and colon mucosal lesions," Gastrointestinal Endoscopy, 1993 vol. 39, No. 1, pp. 58-62.

Johnston et al., "Endoscopic spray cryotherapy: a new technique for mucosal ablation in the esophagus," Gastointestinal Endoscopy, Jul. 1999, vol. 50, pp. 86-92.

L. Laine, "Determination of the Optimal Technique for Bipolar Electrocoagulation Treatment," Gastroenterology, 1991, vol. 100, pp. 107-112.

B. Overholt, "Photodynamic therapy for Barrett's esophagus: follow-up in 100 patients," Gastrointestinal Endoscopy, 1999, vol. 49, No. 1, pp. 1-7.

Salo et al., "Treatment of Barrett's Esophagus by Endoscopic Laser Ablation and Antireflux Surgery," Annals of Surgery, vol. 227, No. 1, pp. 40-44.

T. V. Taylor et al., "Ablation of neoplasia by direct current," Br. J. Cancer, 1994, vol. 70, pp. 342-345.

J. van den Boogert, "Photodynamic Therapy for Esophageal Lesions: Selectivity Depends on Wavelength, Power, and Light Dose," The Society of Thoracic Surgeons, Nov. 1999, vol. 68, Issue 5, pp. 1763-1769.

International Search Report dated Sep. 27, 2012 for International Application No. PCT/US2012/050899.

International Written Opinion dated Sep. 27, 2012 for International Application No. PCT/US2012/050899.

* cited by examiner

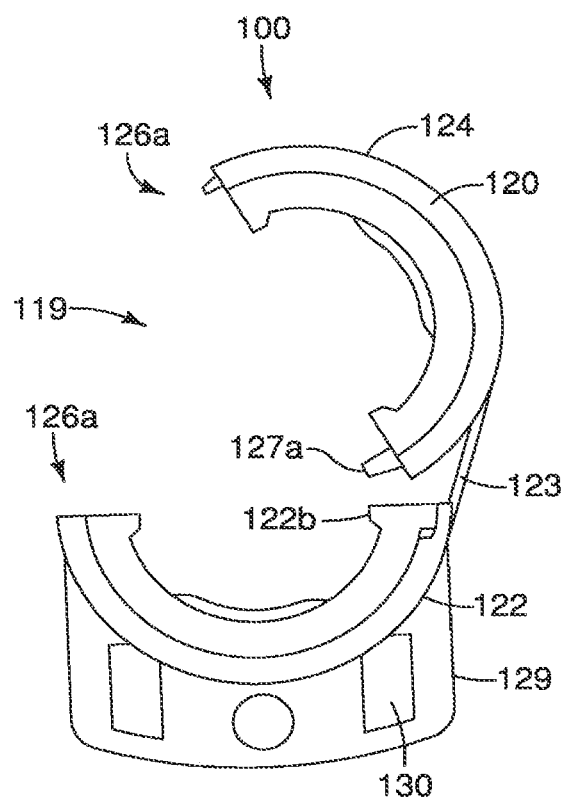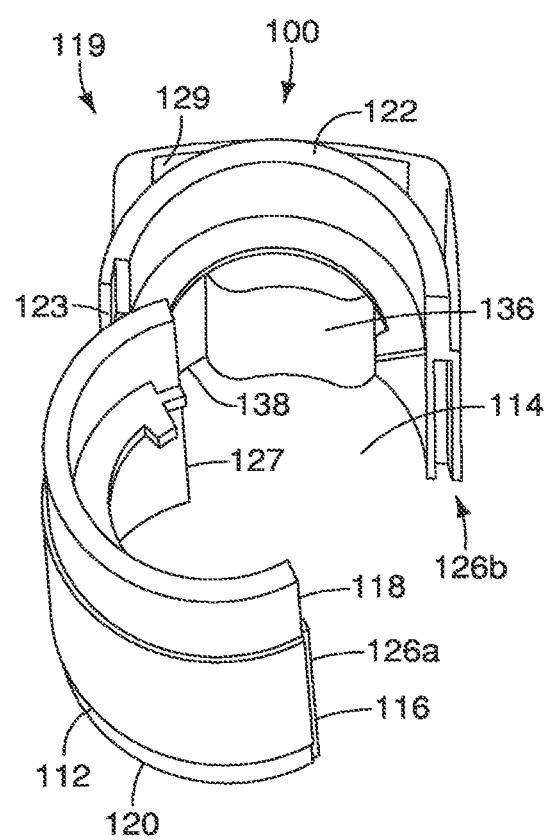
FIG. 5
FIG. 6

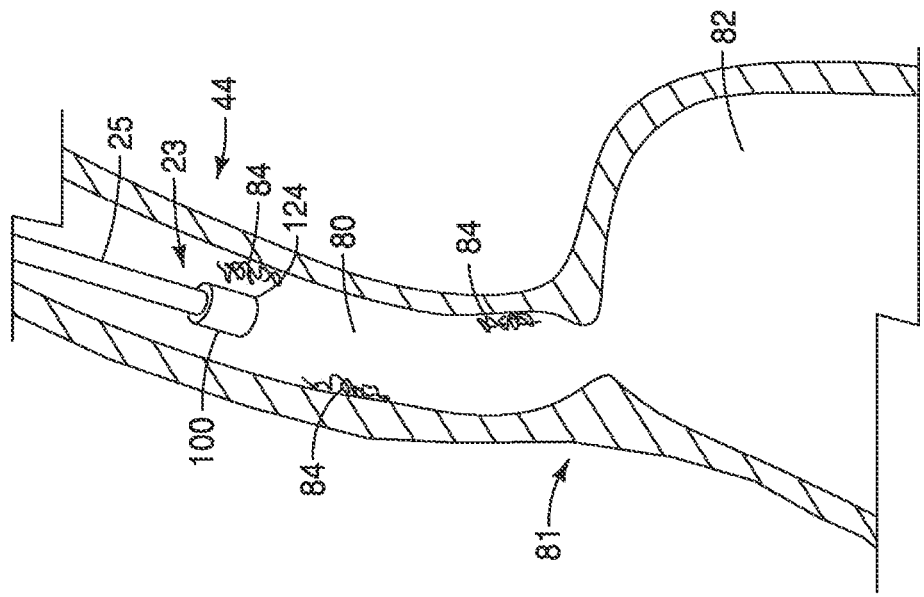
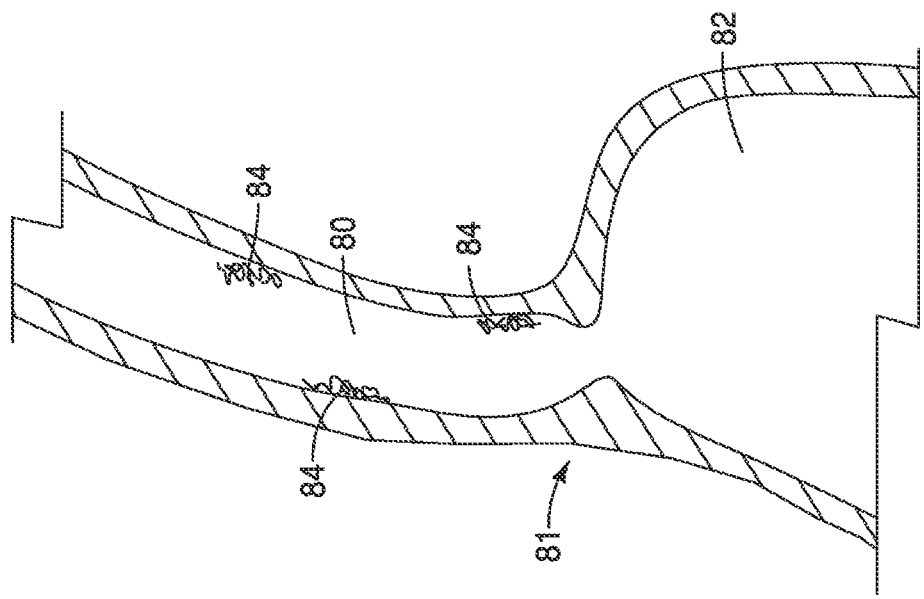

CAP FOR ATTACHMENT TO AN ENDOSCOPE

RELATED APPLICATIONS

This application is a continuation of U.S. patent application Ser. No. 13/586,643, filed on Aug. 15, 2012, which claims the benefit of U.S. Provisional Application No. 61/525,380, filed Aug 19, 2011, each of which is incorporated by reference herein in its entirety.

TECHNICAL FIELD

This invention generally relates to cap for attachment to an endoscope, and in particular to a multipart cap for attachment to an endoscope.

BACKGROUND

Endoscopic devices and procedures may be used to diagnose, monitor and treat various conditions by close examination of the internal organs. By way of background, a conventional endoscope generally is an instrument having a device for visualizing the interior of an internal region of a body and a lumen for inserting one or more treatment devices therethrough. A wide range of applications have been developed for the general field of endoscopes including by way of non-limiting example the following: arthroscope, angioscope, bronchoscope, choledochoscope, colonoscope, cytoscope, duodenoscope, enteroscope, esophagogastroduodenoscope (gastroscope), laparoscope, laryngoscope, nasopharyngo-neproscope, sigmoidoscope, thoracoscope, and utererscope (individually and collectively, "endoscope").

In some procedures, it may be necessary to attach a medical device to a distal end of an endoscope and extend the medical device distal to the distal end. Endoscopes manufactured by different companies or for insertion in different areas within the patient may have different diameters at the distal end of the endoscope. The different diameters require that each medical device to be connected to the distal end of the endoscope have the appropriate diameter to fit with the diameter of the particular endoscope being used for the procedure. The requirement for different diameters on a variety of different types of medical devices greatly increases the need for increased inventory of the medical devices, depending on the type of endoscope that will be used during a medical procedure. The increased inventory also increases the costs associated with these medical procedures.

It is desirable to have a cap portion that is universally connectable to many different diameter endoscopes.

By way of non-limiting example, it may be desirable to have a cap portion that is suitable for treatment of Barrett's Esophagus. Endoscopic treatment of Barrett's esophagus includes endoscopic mucosal resection (EMR). One method of performing EMR involves ablation of the mucosal surface by heating the surface until the surface layer is no longer viable. The dead tissue is then removed.

Treatment devices for performing EMR have been developed using bipolar ablation technology that includes positioning a probe against the target tissue and delivering energy to the tissue to ablate the tissue in contact with the probe. It is desirable to have a treatment device that fits onto a variety of different diameter endoscopes, that is simple to use, that minimizes the number of steps and time required for a treatment procedure and that provides treatment under direct endoscopic visualization.

BRIEF SUMMARY

Accordingly, it is an object of the present invention to provide a device and a method having features that resolve or improve on one or more of the above-described drawbacks.

In one aspect, a cap dimensioned and otherwise configured for attachment to a distal end of an endoscope is provided. The cap includes a tubular body having a proximal portion, a distal portion and a lumen extending therethrough. The proximal portion includes a first portion and a second portion where at least one of the first portion and the second portion includes a connector for operably connecting the first portion and the second portion. The cap has in open configuration wherein at least a portion of the first portion and the second portion are spaced apart and movable relative to each other. The cap also has a closed configuration wherein the first and second portions are connected and the lumen if formed therethrough. The cap in the closed configuration is sized and shaped to be positionable on the distal end of the endoscope.

In another aspect, a method of positioning a cap on a distal end of an endoscope is provided. The method includes positioning a first portion of a proximal portion of a tubular body against the distal end of the endoscope and moving a second portion of the proximal portion of the tubular body in proximity to the first portion. The method further includes joining the first portion and the second portion together with a connector and securing the proximal portion of the tubular body to the endoscope so that a distal portion of the tubular body extends distal to the distal end of the endoscope.

Advantages of the present invention will become more apparent to those skilled in the art from the following description of the preferred embodiments of the invention which have been shown and described by way of illustration. As will be realized, the invention is capable of other and different embodiments, and its details are capable of modification in various respects. Accordingly, the drawings and description are to be regarded as illustrative in nature and not as restrictive.

BRIEF DESCRIPTION OF THE DRAWINGS

FIG. 5 is an end view of a cap for attachment to a distal end of an endoscope in accordance with an embodiment of the present invention in an open configuration;

FIG. 6 is a perspective view of the cap shown in FIG. 5;

FIGS. 19A-19C illustrate operation of an embodiment of a cap.

DETAILED DESCRIPTION

Figure 1:
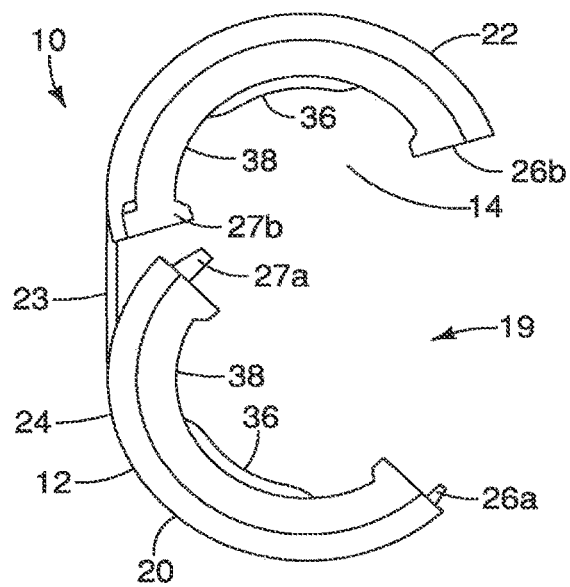
FIG. 1 is an end view of a cap for attachment to a distal end of an endoscope in accordance with an embodiment of the present invention.

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering the cap to a patient. Hence the term "distal" means the portion of the cap that is farthest from the physician and the term "proximal" means the portion of the cap that is nearest to the physician.

Figure 2:
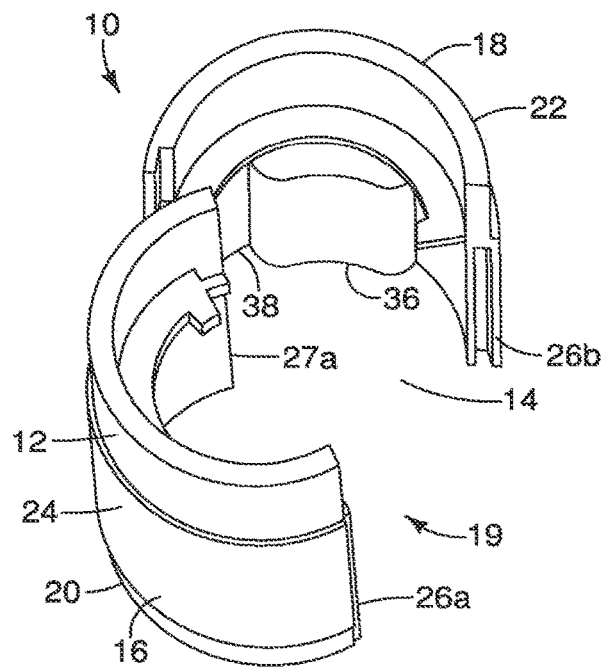
FIG. 2 is a perspective view of the cap shown in FIG. 1.

FIGS. 1 and 2 illustrate an embodiment of a cap 10 in accordance with an embodiment of the present invention. As shown in FIGS. 1 and 2, the cap 10 includes a tubular body 12 having a lumen 14 formed therein. The cap 10 includes a proximal portion 16 and a distal portion 18 as shown in FIG. 2. The proximal portion 16 of the cap 10 is sized to fit on a distal end 23 of an endoscope 25 (see FIGS. 8 and 9 showing the cap positioned on the endoscope). The cap 10 is shown in an open configuration 19 in FIGS. 1 and 2.

Figure 3:
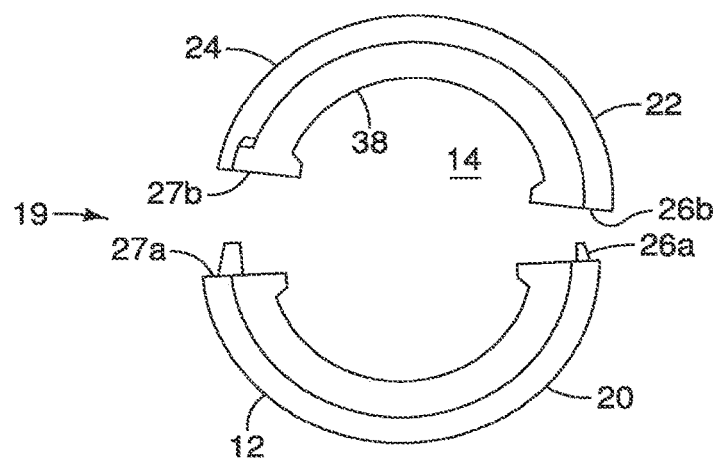
FIG. 3 is an end view of an embodiment of a cap for attachment to a distal end of an endoscope in accordance with an embodiment of the present invention in an open configuration.

In some embodiments, the cap 10 may include a first portion 20, a second portion 22 and a connector such as a hinge portion 23 that connects the first and second portions 20, 22 and that allows the cap 10 to be positioned on the distal end of the endoscope 25 without sliding the cap 10 over the endoscope 25. The hinge portion described herein may be any type of hinge known to one skilled in the art, including, but not limited to hinges that pivot about a fixed axis of rotation, living hinges, floating hinges and the like. In some embodiments, the cap 10 may be slid over the endoscope 25. The cap 10 may be designed so that an inner diameter of the cap 10 is sized to fit on the endoscope 25 and have a slightly larger outer diameter at the connection than an outer diameter of the endoscope 25. The first portion 20 and the second portion 22 may be curvilinear in shape, for example forming two semicircular portions, so that when the first and second portions 20, 22 are connected a cylindrical tube having an inner diameter that fits on the distal end 23 of the endoscope 25 is formed. Other non-cylindrical shapes may also be used providing the cap 10 fits on a similarly shaped distal end 23 of the endoscope 25. The first and second portions 20, 22 may be connected by a connector 26 having a first member 26a on the first portion 20 and a second member 26b on the second portion 22 that join together to close the cap 10. By way of non-limiting example, the connector 26 may be a snap-fit connection. The connector 26 may be releasably connected. The first and second portions 20, 22 of the cap 10 may also be connected with a second connector 27. The second connector 27 may include a first member 27a on the first portion 20 and a second member 27b on the second portion 22. The second connector 27 may be similar to the connector 26 or the second connector 27 may be different. By way of non-limiting example, the second connector 27 may be used to align the first and second portions 20, 22 using a protrusion and groove configuration where one of the first and second members 27a, 27b includes a protrusion and the other of the first and second members 27a, 27b includes a groove sized and shaped to receive the protrusion. In some embodiments, the first and second portions 20, 22 may be separate portions without a hinge and connected together by connectors 26 and 27 as shown in FIG. 3.

Figure 4:
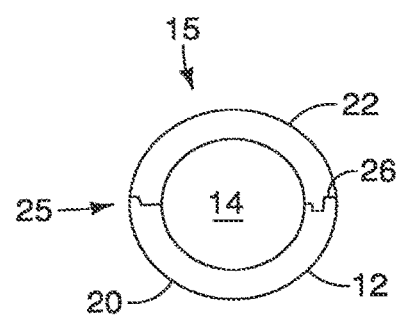
FIG. 4 is an end view of the cap shown in FIG. 3 in a closed configuration.

In some embodiments, the cap 10 may include a pad portion 36 positioned on an interior wall 38 of the body 12 within the lumen 14 as shown in FIGS. 1 and 2. The pad portion 36 may be included to facilitate securing the cap 10 on the endoscope 25. The pad portion 36 may be used when the cap 10 is designed to fit on different endoscopes having a different diameter distal end. The size and shape of the pad portion 36 may be varied depending on the type of endoscope on which the cap 10 is placed. In some embodiments, several pad portions 36 may be used. The pad portion 36 may be deformable to press against the endoscope 25 when the cap 10 is in a closed position 15. The closed position 15 is shown in FIG. 4. The pad portion 36 may be made from any kind of material and in some embodiments, the pad portion 36 may be formed from a material that increases the frictional fit against the endoscope.

The distal portion 18 of the cap 10 may extend beyond the distal end 23 of the endoscope 25. In some embodiments, the distal portion 18 may be formed from a material having sufficient transparency so that the operator using an optical port of the endoscope 25 may view through a wall 24 the distal portion 18 to observe a portion of a tissue to be treated with a medical device provided with the cap 10.

Figure 7:
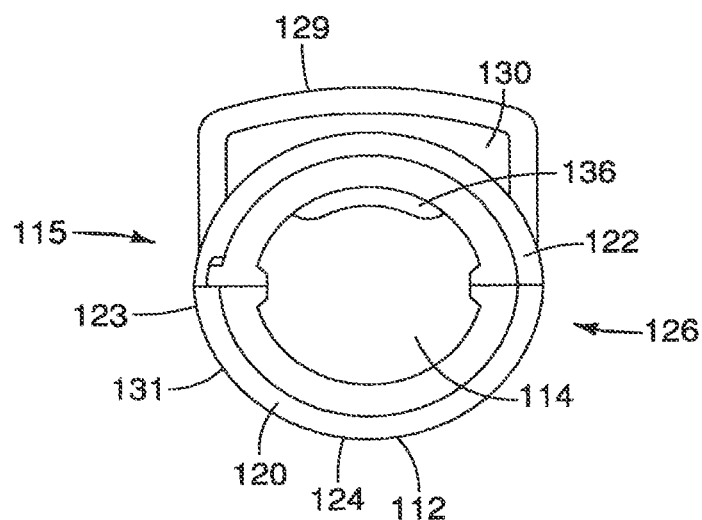
FIG. 7 is an end view of the cap shown in FIG. 5 in a closed configuration.

The cap for attachment to an endoscope may be provided for use with different types of medical devices. In an exemplary embodiment, a cap 100 may include some or all of the elements of the cap 10. In some embodiments, the cap 100 may be provided for use with an electrode for ablating tissue within a patient's lumen. The cap 100 is illustrated in FIGS. 5-7 and includes a cover portion 129 forming a recess 130 as part of the cap 100. The cover portion 129 may be integrally formed with the cap 100 or provided a separate piece and connected to the cap 100. The recess 130 of the cover portion 129 may be sized and shaped to hold an extendable electrode portion 134 within the recess 130. The electrode 134 is described in more detail below.

As shown in FIGS. 5-7, the cap 100 includes a tubular body 112 having a lumen 114 formed therein. The cap 100 includes a proximal portion 116 and a distal portion 118. The proximal portion 116 of the cap 100 is sized to fit on the distal end 23 of the endoscope 25. The cap 100 is shown in an open configuration 119 in FIGS. 5 and 6 and in a closed configuration 115 in FIG. 7.

In some embodiments, the cap 100 may include a first portion 120, a second portion 122 and connector such as a hinge portion 123 that connects the first and second portions 120, 122 and that allows the cap 100 to be positioned on the distal end 23 of the endoscope 25 without sliding the cap 100 over the endoscope. In other embodiments, the first portion 120 and the second portion 122 may be separate portions without a hinge. The cap 100 may be designed so that an inner diameter of the cap 100 tightly fits on the endoscope 25. The first and second portions 120, 122 may be connected by a connector 126 having a first member 126a on the first portion 120 and a second member 126b on the second portion 122 that join together to close the cap 100. As shown in FIG. 7, when the cap 100 is in the closed configuration 115, a cylindrical cap is formed having a substantially smooth outer surface 131.

By way of non-limiting example, the connector 126 may be a snap-fit connection. The first and second portions 120, 122 of the cap 100 may also be connected with a second connector 127. The second connector 127 may include a first member 127a on the first portion 120 and a second member 127b on the second portion 122. The second connector 127 may be similar to the connector 126 or the second connector 127 may be different. By way of non-limiting example, the second connector 127 may be used to align the first and second portions 120, 122 using a protrusion and groove configuration where one of the first and second members 27a, 127b includes a protrusion and the other of the first and second members 127a, 127b includes a groove sized and shaped to receive the protrusion.

As shown in FIG. 6, some embodiments of the cap 100 may include a pad portion 136 positioned on an interior wall 138 of the body 112 within the lumen 114. The pad portion 136 may be included to facilitate securing the cap 100 on the endoscope 25. The pad portion 136 may be used when the cap 100 is designed to fit on different endoscopes having a different diameter distal end. The size and shape of the pad portion 136 may be varied depending on the type of endoscope on which the cap 100 is placed. In some embodiments, several pad portions 136 may be used. The pad portion 136 may be deformable to press against the endoscope when the cap 100 is in the closed configuration 115. The pad portion 136 may be made from any kind of material and in some embodiments, the pad portion 136 may be formed from a material that increases the frictional fit against the endoscope 25.

The distal portion 118 of the cap 100 may extend beyond the distal end 23 of the endoscope 25. In some embodiments, the distal portion 118 may be formed from a material having sufficient transparency so that the operator using an optical port of the endoscope 25 may view through a wall 124 the distal portion 118 to observe a portion of a tissue to be treated with a medical device provided with the cap 100.

Figure 8A:
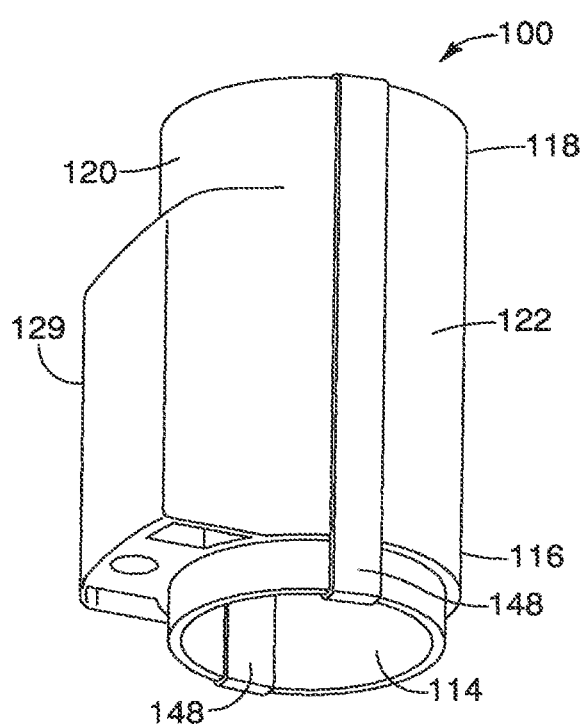
FIGS. 8A-8C illustrate an embodiment of a cap in accordance with the present invention.
Figure 8B:
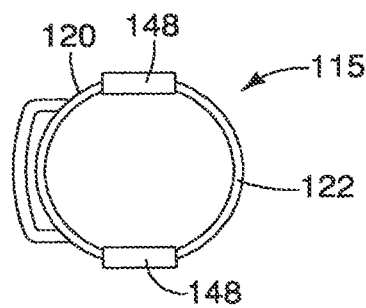
Figure 8C:
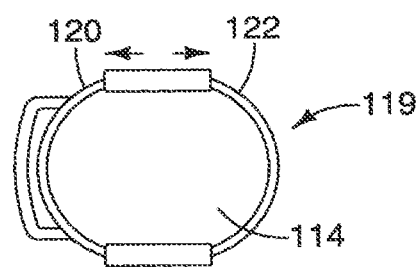
Figure 9:
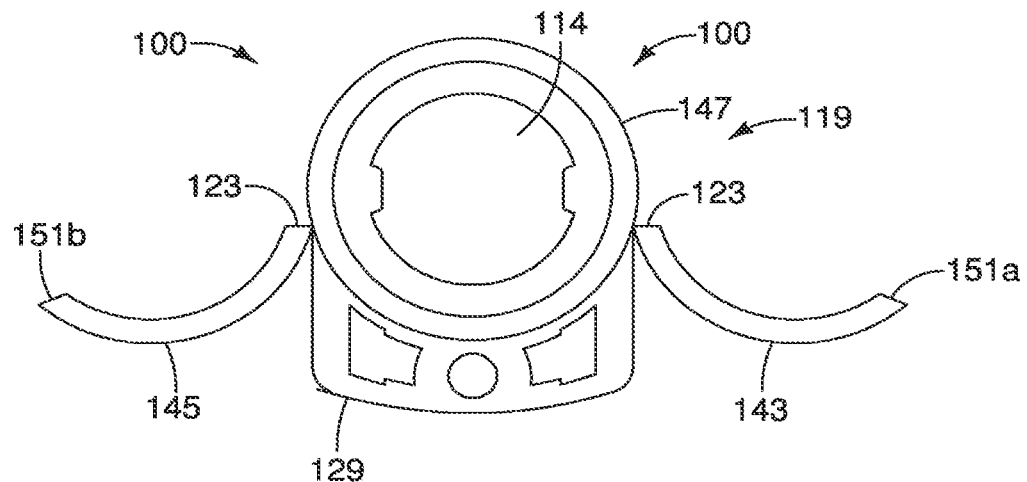
FIG. 9 is an end view of an embodiment of a cap in an open configuration.

FIGS. 8A-8C illustrate an embodiment of the cap 100 having at least one elastomeric connector 148 and may include any of the other elements described herein. Any of the embodiments described herein may include one or more elastomeric connectors instead of the connectors such as the hinge or the snap fit connections. As shown in FIG. 8A, the connector 148 may extend longitudinally from the proximal portion 116 to the distal portion 118 of the cap 100. The connector 148 connects the first portion 120 to the second portion 122. The connector 148 is sufficiently flexible to allow the connector 148 to be expanded to the open configuration 119 shown in FIG. 8C so the cap 100 may be slid over the endoscope 25. The connector 148 then allows the cap 100 to return to the closed configuration 115 shown in FIG. 8B so that the cap 100 is securely positioned on the endoscope 25 and the medical procedure can be performed. The connector 148 may be formed from any material having sufficient elasticity to allow the cap 100 to be moved to the expanded configuration 119 and to elastically return to the closed configuration 115. As shown in FIG. 8A, the cap 100 includes two elastomeric connectors 148. In some embodiments, the cap 100 may include a single elastomeric connector 148 and may also include a hinge or other connector.

Figure 10:
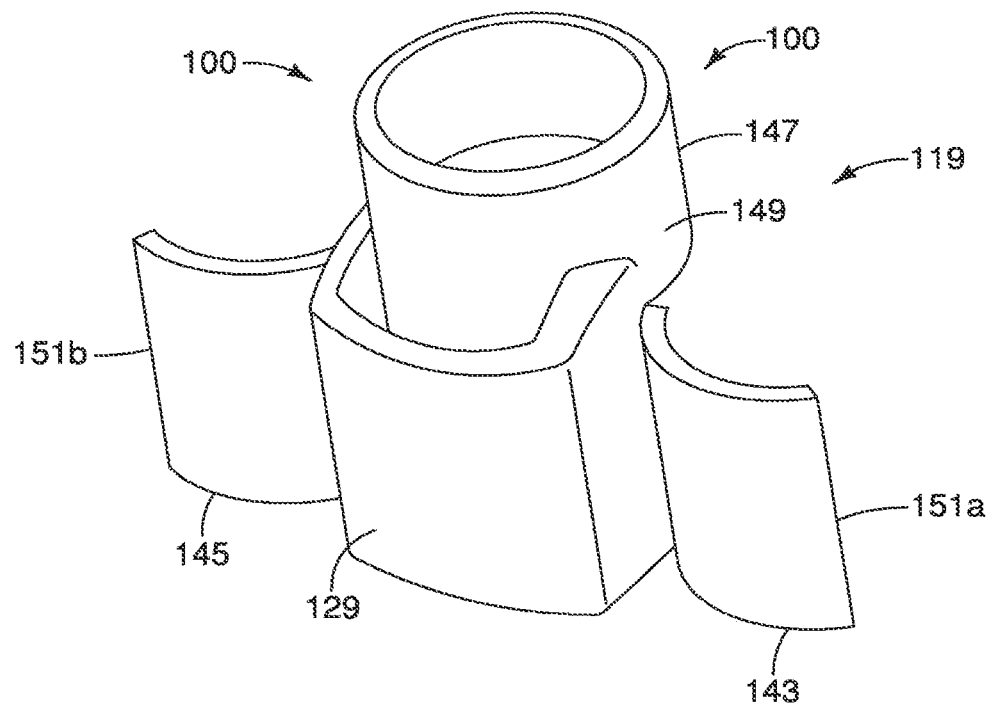
FIG. 10 is a perspective view of the cap shown in FIG. 9.

FIGS. 9 and 10 illustrate an embodiment of the cap 100 similar to the caps described above and having two connectors provided in the form of hinges 123. The cap 100 includes a first portion 143 and a second portion 147 movably connected to the hinges 123. FIGS. 9 and 10 illustrate the cap 100 in the open configuration 119. The closed 115 configuration is similar to that shown in FIG. 7. In the closed configuration 115, the first portion 135 is connected to the second portion 145 at a connector 151. The connector 151 may include mating portions 151a, 151b that mate together when the first and second portions 143, 145 are connected. The cap 100 shown in FIGS. 9 and 10 also includes a third portion 147 operably connected to the first and second portions 143, 145 to form the tubular body 112. The third portion 147 may include a tubular portion 149 that maintains the tubular shape in the open and the closed configurations 119, 115.

Figure 11:
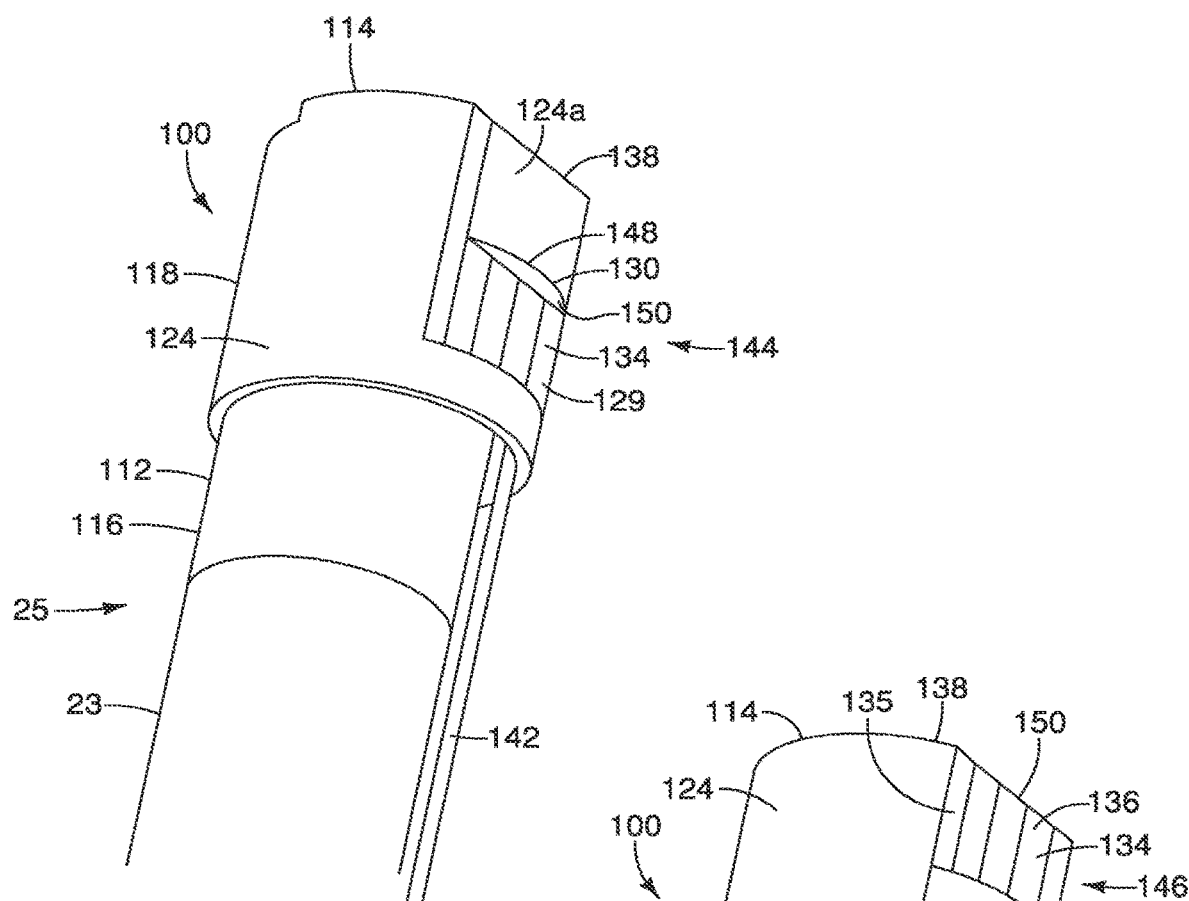
FIG. 11 is a perspective view of a cap with an electrode portion in a covered position on a distal end of an endoscope in accordance with an embodiment of the present invention.
Figure 12:
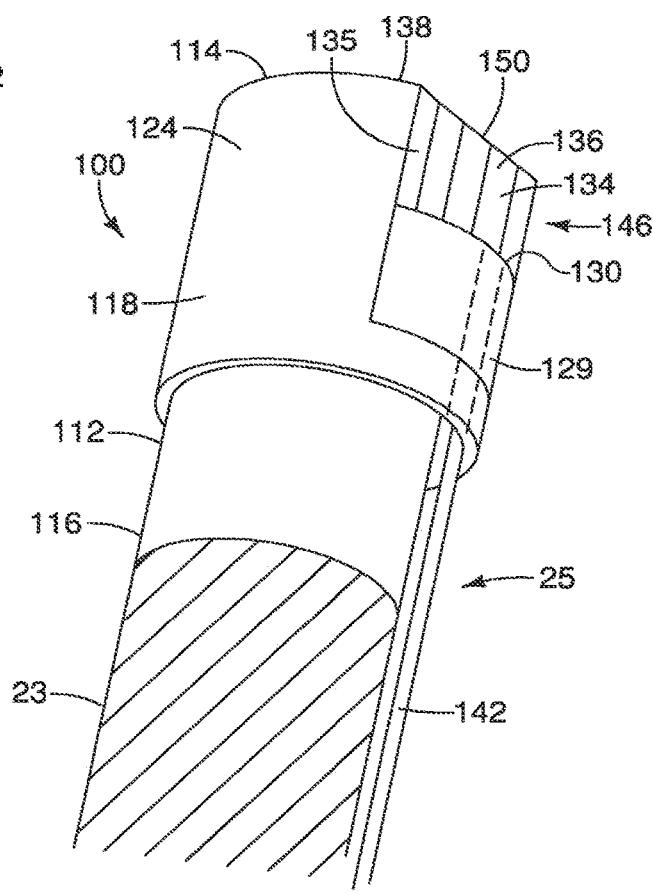
FIG. 12 is a perspective view of the cap shown in FIG. 11 with the electrode portion in an exposed position.

A cover portion 129 is illustrated in FIGS. 5-12 and may be integrally formed with the cap 100 or provided as a separate portion and connected to the cap 100. The cover portion 129 is at least partially spaced apart from the tubular body 112 to form the recess 130. The recess 130 may be sized and shaped to hold the extendable electrode portion 134 within the recess 130 in a covered position 144 as shown in FIG. 11 with the cap 100 positioned on the distal portion 23 of the endoscope 25. The electrode portion 134 is slidably positionable within the recess 130 of the cover portion 129. In some embodiments, the electrode portion 134 may be positioned entirely within the recess 130 of the cover portion 129 in the covered position 144 so that electrodes positioned on the electrode portion 134 are completely covered. As shown in FIG. 12, the electrode portion 134 may be extended distally from the recess 130 so that at least a portion of a surface 135 of the electrode portion is exposed and can contact the tissue to be treated. A portion 124a of the wall 124 is positioned behind the electrode portion 134 when the electrode portion 134 is an exposed position 146 and may be used to support the electrode portion 134 when the electrode portion 134 is pressed against the tissue to be treated. In some embodiments, a distal end 136 of the electrode portion 134 does not extend beyond a distal end 138 of the distal portion 118 of the cap 100.

As shown in FIGS. 11 and 12, the electrode portion 134 may be connected to a drive catheter 142 that extends proximally from the electrode portion 134 to a proximal control handle (not shown). The drive catheter 142 is distally movable to extend the electrode portion 134 from the recess 130 of the cover portion 129 and proximally movable to re-position the electrode portion 134 within the recess 130. Typically, the electrode portion 134 is positioned within the recess 130 of the cover portion 129 when the cap 100 is being delivered to a treatment site or being repositioned within a patient's lumen for additional treatment at one or more additional sites. Positioning of the electrode portion 134 within the recess 130 also helps to prevent accidental energy delivery, for example to healthy tissue. The electrode portion 134 is at least partially distally extended from the recess 130 of the cover portion 29 for treatment at a site and energy is delivered to the tissue to ablate the diseased tissue as described in more detail below.

In some embodiments, the electrode portion 134 may include a beveled portion 148 on a distal end 150 of the electrode portion 134 as shown in FIG. 11. Movement of the drive catheter 142 proximally and distally may be used to facilitate the scraping of tissue. In addition, movement of the endoscope 25 proximally and distally may also be used to facilitate the scraping. The beveled portion 148 may be used to scrape treated tissue to help remove the tissue after treatment.

Figure 13:
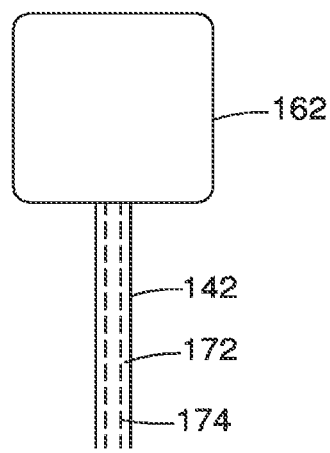
FIG. 13 is a partial view of an embodiment of a support member of the ablation cap.
Figure 14:
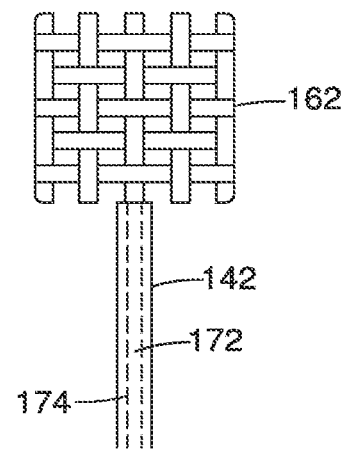
FIG. 14 is a partial view of an embodiment of a support member of the ablation cap.

The electrode portion 134 may include a support member 62 upon which one or more electrodes 64 are positioned. FIGS. 13 and 14 illustrate exemplary support members 162. As shown in FIG. 13, the support member 162 may be a solid material, such as a plastic material. As shown in FIG. 14, the support member 162, may be a mesh. When the solid material or the mesh is formed of a metallic material, a layer of insulation may be provided between the support member 162 and the electrodes 164. The support member 162 may be moved proximally and distally with the drive catheter 142. The electrodes 164 may be secured to the support member 162 by any method know to one skilled in the art. By way of non-limiting example, the electrodes may be secured by gluing, bonding, taping, an adhesive backing on the electrodes, crimping, manufacturing the electrodes directly on to the body and the like.

Electrical wires 172 may extend through a lumen 174 of the drive catheter 142 as shown in FIGS. 13 and 14 and connect to the electrodes 164 to supply the energy for ablation. Alternatively, the electrical wires 172 may extend through a lumen of the endoscope 25. The electrodes 164 may be seen in FIGS. 15 and 16. The electrodes 164 may be provided separately from the support member 162 and in some embodiments may also form the support member 162 without providing a separate support member.

Figure 15:
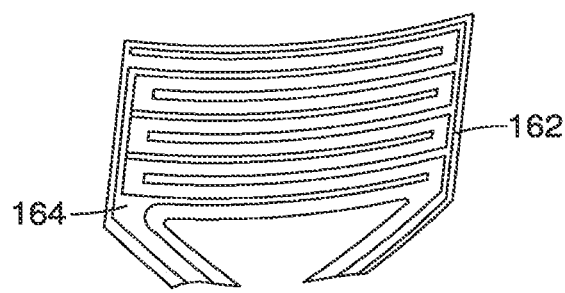
FIG. 15 illustrates an embodiment of an electrode of the ablation cap.
Figure 16:
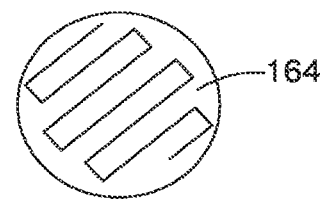
FIG. 16 illustrates an embodiment of an electrode of the ablation cap.

As shown In FIGS. 15 and 16, the electrodes 164 may include positive electrodes 164 and negative electrodes 164 in a bipolar device and when provided as a bipolar device the electrodes 164 are provided in pairs, one positive and one negative electrode per pair. The electrodes 164 may also be provided as a monopolar device having a single electrode 164 or a plurality of electrodes 164 with a grounding pad or an impedance circuit additionally provided (not shown). The electrodes 164 may be provided in any pattern on the support member 162. The electrodes 164 may cover the entire support member 164 or a portion thereof. By way of non-limiting example, a space 162 between the positive electrode portion 164 and the negative electrode portion 164 may between about 0.1 mm to about 5 mm. In some embodiments, the energy may be delivered to the tissue for a period of time from about 0.1 second to about 10 seconds. In some embodiments, the amount of energy delivered to the tissue may be from about 10 watts to about 60 watts. Other spacing distances between electrodes, length of time, and energy delivery are also possible and depend on the target tissue, the depth of the lesion, the type of energy, the length of application of the energy to the tissue and the spacing of the electrodes.

The electrodes 164 are operably connected to an energy source (not shown). In some embodiments, the energy source may be a radio frequency source. However, other types of energy sources may also be used to provide energy to the electrodes. By way of non-limiting example, additional possible energy sources may include microwave, ultraviolet, cryogenic and laser energies.

Figure 17:
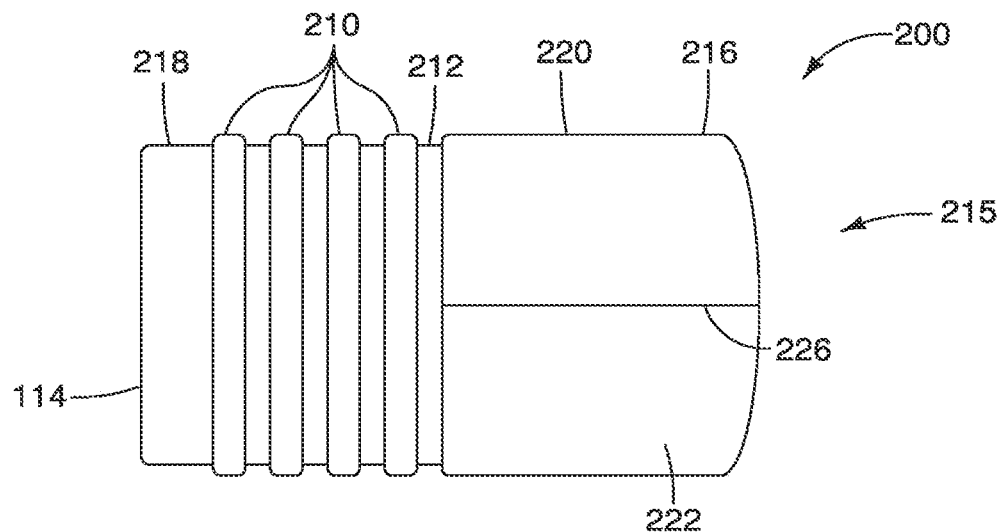
FIG. 17 is a side view of an embodiment of a cap including a plurality of ligating bands in a closed configuration in accordance with the present invention.
Figure 18:
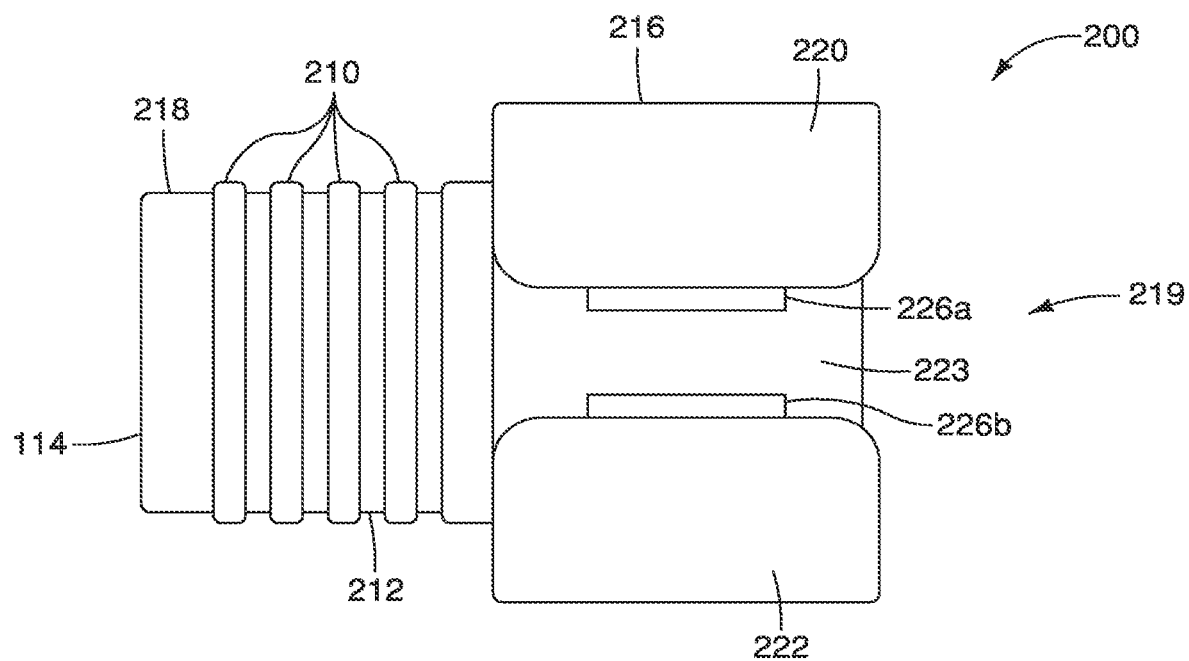
FIG. 18 is a side view of the cap shown in FIG. 17 in an open configuration.

In some embodiments, a cap 200 may be provided to deliver a plurality of ligating bands 210 to a patient's lumen. The cap 200 may include some or all of the elements of the cap 10 and/or the cap 100 described above. As shown in FIGS. 14 and 15, the cap 200 includes a body 212 having a lumen 214 formed therein. The body 212 includes a proximal portion 216 and a distal portion 218. The proximal portion 216 of the cap 200 is sized to fit on the distal end 20 of the endoscope 22. The cap 200 is shown in a closed configuration 215 in FIG. 17 and in an open configuration 219 in FIG. 18. The distal portion 218 including the ligating bands 210 remains fixed in position with the bands 210 encircling the distal portion 218 of the cap 200. The proximal portion 216 is movable between the open configuration 219 and the closed configuration 215 to secure the cap 200 to the endoscope 25.

Similar to the embodiments described above, the cap 200 includes a first portion 220 and a second portion 222. The cap portion 200 may include a hinge portion 223 that connects the first and second portions 220, 222 and that allows the cap 200 to be positioned on the distal end 23 of the endoscope 25 without sliding the cap 200 over the endoscope. The cap 200 may be designed so that an inner diameter of the cap 200 tightly fits on the endoscope. The first and second portions 220, 222 may be connected by a connector 226 having a first member 226a on the first portion 220 and a second member 226b on the second portion 222 that join together to close the cap 200 similar to the connector described above. A second connector 227 may also be included similar to the second connector described above. In some embodiments, the first and second portions 220, 222 may be separate portions without a hinge and connected together by one or more connectors 226 and 227. The distal portion 218 may be connected to the first portion 220, the second portion 222 or both when the cap 200 is in the open configuration 219. The cap 200 may also include a pad portion similar to the pad portion described above. Additional details regarding operation and additional features of the cap including a plurality of ligating band are available in U.S. Pat. No. 6,685,713.

The cap of the present invention may also be used together with other medical devices that are typically connected to an endoscope at the distal end of the endoscope. By way of non-limiting example, a cap having a first portion and a second portion that are connectable to fit on the distal end of an endoscope may also include a suction port, a wore guide port for a short wire device, an extended channel, for example for a biopsy forceps and the like.

In some embodiments, the cap may be made primarily of a substantially transparent or translucent polymer such as polytetrafluoroethylene (PTFE). Additional possible materials include, but are not limited to the following, polyethylene ether ketone (PEEK), fluorinated ethylene propylene (FEP), perfluoroalkoxy polymer resin (PFA), polyamide, polyurethane, high density or low density polyethylene, and nylon. In some embodiments, the cap may be formed from a lubricious material such as PTFE and the like for easy slidability within the patient's lumen for delivery to the treatment site. The cap or a portion thereof may also be coated or impregnated with other compounds and materials to achieve the desired properties. Exemplary coatings or additives include, but are not limited to, parylene, glass fillers, silicone hydrogel polymers and hydrophilic coatings.

Operation of the cap using the cap 100 as a non-limiting example is explained. The cap 100 may be connected to the endoscope 25 by positioning the first portion 120 or the second portion 22 against the distal end 23 of the endoscope 25 with the cap 100 in the open configuration 119. One or more pad portions 136 may be positioned between the distal end 23 of the endoscope 25 and the first or second portion 120, 122. The first portion 120 and the second portion 122 are aligned and the connector 126 is connected to join the first portion 120 to the second portion 122 while securing the cap 10 to the distal end 23 of the endoscope 25 in the closed configuration 115. When the cap 100 includes the hinge 123, the hinge 123 may be moved to bring the first portion 120 into contact with the second portion 122. Portions of the medical device such as the drive cable 142 and the wires 172 may be connected to the proximal end of the endoscope or the electrical connection before or after the cap 100 is secured to the endoscope 25. In embodiments of the cap 100 including an elastomeric connector 148, the first portion 120 and the second portion 122 are pulled to the open configuration 119 so that the inner diameter of the tubular portion is greater than the endoscope. The cap 100 is slid over the endoscope 25 and the elastomeric connector 148 returns to the closed configuration 115

Figure 19C:
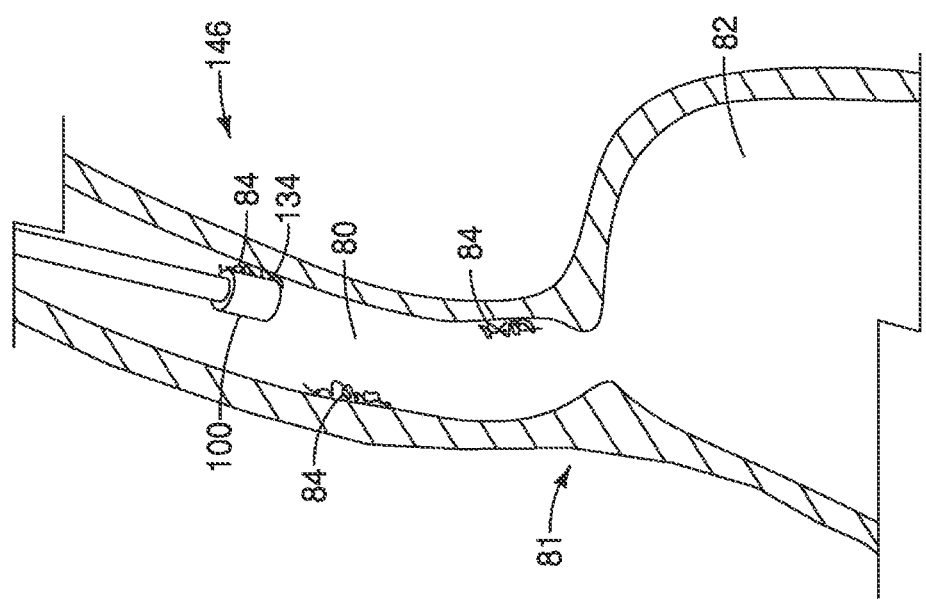

Once the cap 100 is secured to the distal end 23 of the endoscope 25, the cap 100 may be delivered to the patient as shown with reference to FIGS. 19A-19C. FIG. 19A illustrates a patient's esophagus 80, lower esophageal sphincter (LES) 81 and stomach 82. Areas of diseased tissue 84 within the esophagus 80 are also shown. The diseased tissue 84 may be columnar mucosa (Barrett's esophagus) that is to be ablated using the cap 100. FIG. 19B illustrates the cap 100 positioned on the distal end 23 of the endoscope 25 and the cap 100 and the endoscope 25 being inserted into the patient's esophagus 80. The cap 100 is positioned in the esophagus 80 near the portion of the diseased tissue 84 to be treated. The insertion of the cap 100 may be monitored using the viewing port of the endoscope 25 and viewed through the wall 124 of the cap 100 to help position the cap 100 at the diseased tissue. As shown in FIG. 19B, the cap 100 is positioned near the diseased tissue 84. While the ablation cap 100 is being positioned, the electrode portion 134 may be in the covered position 144. As shown in FIG. 19C, the diseased tissue 84 is in contact with the electrode portion 134 in the exposed position 146 so that the electrodes 64 are in contact with the diseased tissue 84 to deliver energy to the diseased tissue 84 to ablate the diseased tissue 84. A power source (not shown) is activated for a sufficient time to ablate the diseased tissue 84. The ablation cap 100 may be repositioned near another portion of diseased tissue 84 for treatment and the steps repeated as many times as needed. While the procedure has been described with reference to the ablation of diseased tissue in the esophagus using the cap 100, the location of the treatment is not limited to the esophagus. By way of non-limiting example, portions of the stomach, or the gastrointestinal tract may also be treated using the cap 100.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

I claim:

1. A cap configured for attachment to a distal end of an endoscope, the cap comprising:

a tubular body having a proximal portion, a distal portion, a lumen extending therethrough, the proximal portion comprising:
a first portion and a second portion, at least one of the first portion and the second portion comprising a connector for operably connecting the first portion to the second portion;
the cap having an open configuration wherein at least a portion of the first portion and the second portion are spaced apart and rotatably movable relative to each other and a closed configuration wherein the first and second portions are connected in a manner not rotatably movable relative to each other and dimensioned to engagingly receive the distal end of the endoscope therebetween, and the lumen is formed between the first portion and the second portion, with the cap in the closed configuration being sized and shaped to be positionable on the distal end of the endoscope by receiving and engaging the distal end of the endoscope into a proximal end of the lumen between the first portion and the second portion; and
an electrode portion configured and dimensioned for ablating tissue within a patient's lumen, where the electrode portion is disposed in a recess of the distal portion, which recess is separated from the lumen between the first portion and the second portion, wherein the electrode portion is distally extendable out from the recess of the distal portion such that a distal end of the electrode portion does not extend beyond a distal end of the distal portion of the body.

2. The cap according to claim 1, wherein the cap further comprises a pad portion positionable on an interior wall of the first portion or the second portion to facilitate securing the body to the endoscope.

3. The cap according to claim 1, wherein the connector comprises a hinge connecting the first portion and the second portion.

4. The cap according to claim 1, wherein the connector comprises an elastomeric portion.

5. The cap according to claim 1, wherein the connector comprises a snap fit connector.

6. The cap according to claim 1, wherein at least a portion of the tubular body comprises a transparent material or a translucent material.

7. The cap according to claim 1, wherein the electrode portion is movably positionable relative to a cover portion.

8. The cap according to claim 7, wherein the cover portion is fixed in position on the proximal portion of the tubular body and includes a recess formed between the cover portion and the tubular body.

9. The cap according to claim 8, wherein the first portion and the second portion are connected by a hinge.

10. A method of securing the cap of claim 1 to a distal end of an endoscope, the method comprising:
positioning a first portion of a proximal portion of a tubular body against the distal end of the endoscope;
moving a second portion of the proximal portion of the tubular body in proximity to the first portion;
joining the first portion and the second portion together with a connector; and
securing the proximal portion of the tubular body to the endoscope so that a distal portion of the tubular body extends distal to the distal end of the endoscope.

11. The method according to claim 10, further comprising positioning a pad portion on an interior wall of the first portion of the second portion before securing the tubular body to the distal end of the endoscope.

12. The method according to claim 10, further comprising moving the second portion in proximity to the first portion using a hinge movably connecting the first portion to the second portion.

13. The method according to claim 10, further comprising securing the first portion to the second portion with the connector having a snap-fit connection.

14. The method according to claim 10, further comprising providing the plurality of ligating bands.

\* \* \* \* \*